United States Patent [19]

Wild

[11] Patent Number: 5,352,307
[45] Date of Patent: Oct. 4, 1994

[54] METHOD OF PRODUCING A BREAST PROSTHESIS

[75] Inventor: Helmut F. Wild, Rohrdorf, Fed. Rep. of Germany

[73] Assignee: Amoena-Medizin-Orthopadie-Technik GmbH, Fed. Rep. of Germany

[21] Appl. No.: 975,920

[22] Filed: Nov. 13, 1992

[30] Foreign Application Priority Data

Nov. 14, 1991 [DE] Fed. Rep. of Germany ... 9114201[U]
Nov. 21, 1991 [DE] Fed. Rep. of Germany ... 9114512[U]
Apr. 6, 1992 [DE] Fed. Rep. of Germany ....... 4211542

[51] Int. Cl.$^5$ ............................................. A61F 2/52
[52] U.S. Cl. .................... 156/66; 156/232; 156/245; 156/321; 264/267; 623/7
[58] Field of Search ............... 264/241, 259, 260, 222, 264/DIG. 30, 46.6, 46.8, 261, 266, 267; 156/61, 66, 232, 245, 321; 450/54, 55; 623/7

[56] References Cited

U.S. PATENT DOCUMENTS

| | | | |
|---|---|---|---|
| 4,100,621 | 7/1978 | Ettipio | 2/114 |
| 4,247,351 | 1/1981 | Rechenberg | 623/7 |
| 4,249,975 | 2/1981 | Rechenberg | 264/267 |
| 4,317,241 | 3/1982 | Knoche | 623/7 |
| 4,356,573 | 11/1982 | Knoche | 623/7 |
| 4,426,742 | 1/1984 | Prahl | 623/7 |
| 4,470,857 | 9/1984 | Casalon | 156/66 |
| 4,553,550 | 11/1985 | Hattori | 450/81 |
| 4,633,565 | 1/1987 | DeWoskin | 156/66 |
| 4,637,398 | 1/1987 | Sherwood | 450/54 |
| 4,792,111 | 12/1988 | Taguchi | 249/83 |
| 5,071,433 | 12/1991 | Naestoft et al. | 623/7 |

FOREIGN PATENT DOCUMENTS

| | | |
|---|---|---|
| 0392960 | 10/1990 | European Pat. Off. . |
| 0433636 | 6/1991 | European Pat. Off. . |
| 2701627 | 7/1978 | Fed. Rep. of Germany . |
| 2742394 | 3/1979 | Fed. Rep. of Germany . |
| 2802375 | 7/1979 | Fed. Rep. of Germany . |
| 9107507.6 | 12/1991 | Fed. Rep. of Germany . |
| 2202745 | 10/1988 | United Kingdom ........ 2/52 |
| WO92/15262 | 9/1992 | World Int. Prop. O. ........ 156/66 |

Primary Examiner—Jay H. Woo
Assistant Examiner—Robert B. Davis
Attorney, Agent, or Firm—Jones & Askew

[57] ABSTRACT

The invention relates to a method for producing a breast prosthesis in which a two-component addition cross-linkable soft elastic silicone rubber composition is introduced into a synthetic resin film constituting the inside and the outside of the prosthesis. The synthetic resin film filled with the as yet uncross-linked silicone rubber composition is arranged in a mold and silicone rubber composition is caused to cross-link with the development of heat. In order to improve upon the known method for the production of breast prostheses that the holding members to be attached may simply be arranged on the breast prosthesis and that the finished breast prosthesis has a neat appearance, in accordance with the invention at least one holding element, preferably in the form of an adhesive strip, is applied to the inner side of the breast prosthesis, by the activation of a hot-melt adhesive.

9 Claims, 1 Drawing Sheet

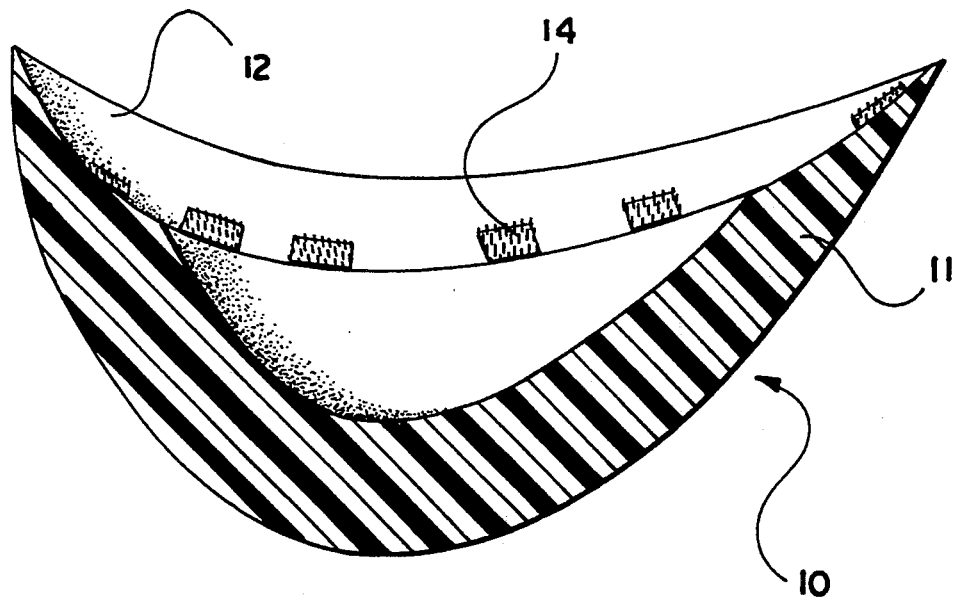
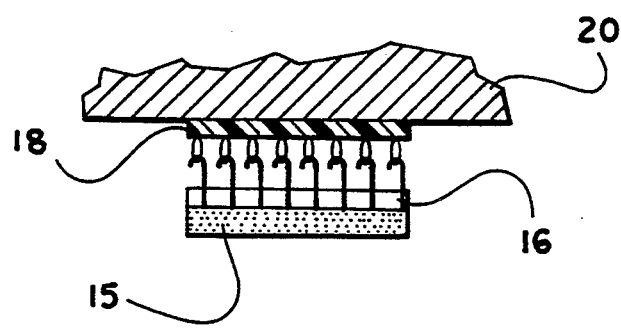

METHOD OF PRODUCING A BREAST PROSTHESIS

The invention relates to a method for producing a breast prosthesis. For the production of breast prostheses it is a known practice to utilize a two-component addition cross-linkable soft elastic silicone rubber composition enveloped in a synthetic resin film constituting the inside and the outside of the prosthesis. Such synthetic resin film filled with the so far non-cross-linked silicone rubber composition is put in a mold with a cover for closing it. The sealed mold is placed in an oven with the silicone rubber composition prior to cross-linking so that the silicone rubber composition can be cross-linked by the application of heat.

A particular problem occurring with breast prostheses, which are for example produced using this method, is that of ensuring that the prosthesis fits on the breast of the wearer snugly and as far as possible free of slip.

In the case of a breast prosthesis proposed in the German patent publication 9,010,426 U attachment is by placing the body of the breast prosthesis in the cups of a brassiere, which may be additionally provided with receiving pockets in order to accommodate the body of the prosthesis.

A satisfactory way of holding a breast prosthesis is possible if the prosthesis is arranged directly on the skin, or on the scar tissue, of the wearer. A prior art breast prosthesis in accordance with the European patent publication 392,960 A of the type initially mentioned has, within an encircling, lip-like edge on its rear side, a surrounding shoulder constituted by a ledge on which adhesive strips or adhesive members are secured, which cooperate with the adhesive zones of strips, which are attached to the skin of the user by a skin-compatible adhesive composition, in such a manner that the breast prosthesis is able to be connected with the holding strips adhering to the skin and to be detached therefrom again. As an attachment means it is preferred to use a burr fastener, for instance a burr fastener material commercially available as VELCRO ®. In the case of these known breast prostheses the holding strips or holding members are stuck to the otherwise complete breast prosthesis by means of a conventional adhesive. In this respect it has turned out to be difficult and complex to correctly position respective adhesive strips or members. An exact positioning is however necessary in order to ensure that there is an exact alignment between the adhesive members on the breast prosthesis and the adhesive members applied to the skin of the wearer using a template. On the other hand the subsequent adhesive attachment using solvent-containing adhesive leads to an unsatisfactory bond involving the formation of corrugations, partial detachment or uneven edges of the bonded adhesive strips or adhesive members.

Accordingly, one object of the invention is to so improve upon the known method for the production of breast prostheses that the holding members to be attached may simply be arranged on the breast prosthesis and that the finished breast prosthesis has a neat appearance.

In accordance with the invention this object is to be attained because, starting with a breast prosthesis of the type initially mentioned, on the synthetic resin film constituting the inner side of the breast prosthesis at least one holding element, and more particularly an adhesive strip, is bonded in place by activation of a hot-melt adhesive. As a consequence of the use of such a hot-melt adhesive a surprisingly neat, flat adhesive bond is produced.

The holding element, of which there is at least one, is best made up of a part of a two-part burr fastener tape.

Such at least one holding element may be bonded to the synthetic resin film by the heat applied during the cross-linking of the silicone rubber composition. In this respect it is consequently possible for the cross-linking heat to be utilized at the same time for activation of the hot-melt adhesive.

The method may be particularly simplified pursuant to a further development of the invention if the holding element, to which the adhesive layer is applied, is positioned by means of a corresponding cooperating member to the mold cover and the cooperating member is arranged at the desired position on the inner side of the breast prosthesis after closing of the mold cover. During the application of heat during the cross-linking of the silicone rubber composition the adhesive layer is activated. The holding element is detached from the cooperating member on the mold cover after cross-linking by opening the mold cover.

The invention furthermore contemplates a form of the method in which the at least one holding element is bonded to the synthetic resin film constituting the inner side of the breast prosthesis with the application of heat prior to introduction of the two-component silicone rubber composition.

Finally, it is moreover possible for the at least one holding element to be bonded to the inner side of the already cross-linked breast prosthesis with the application of heat. In the case of this form of the method as well there is a neat bonding of the holding element to the synthetic resin film.

Preferably both the synthetic resin film utilized and also the hot-melt or thermosetting adhesive include polyurethane.

As a holding element it is possible to employ a permanently tacky layer applied to a support paper or film. Such permanently tacky layers on a synthetic resin basis are known per se. The layers do have the advantage that they render it possible for the breast prosthesis to be adhered to the skin of the user without bits of the adhesive layer remaining on the skin after removing the breast prosthesis again.

In accordance with a particularly advantageous form of the invention there is a provision for the permanently tacky layer to be arranged on a support film whose rear side is able to be connected by a releasable adhesive joined with the complementary adhesive layer of a connecting film bonded to the breast prosthesis. When the permanently tacky layer has lost its tack after a long period of use, it may be pulled off together with its support film and replaced by a new support film bearing a fresh permanently tacky layer.

The holding element may cover practically the entire inner side of the breast prosthesis. This is a particular advantage if comparatively heavy breast prostheses are to be worn.

As an alternative it is possible for the holding element to extend over an edge part of the inner side of the breast prosthesis. It is furthermore possible to bond a plurality of holding elements over the edge part or over the entire surface with a distribution on the inner side of the breast prosthesis.

BRIEF DESCRIPTION OF THE DRAWINGS

FIG. 1 is a side cross-sectional view of a breast prosthesis with holding elements attached thereto according to the invention.

FIG. 2 is a partial cross sectional view of a mold cover showing a holding element temporarily secured thereto.

DETAILED DESCRIPTION OF THE PREFERRED EMBODIMENT

In accordance with the invention FIG. 1 shows a breast prosthesis 10 of the type initially mentioned, and on the synthetic resin film 12 constituting the inner side of the breast prosthesis at least one holding element 14, and more particularly an adhesive strip, is bonded in place by activation of a hot-melt adhesive 15. As a consequence of the use of such a hot-melt adhesive a surprisingly neat, flat adhesive bond is produced.

The holding element 14, of which there is at least one, is best made up of a hook part of a two-part burr fastener tape 16, best shown in FIG. 2.

Such at least one holding element 14 may be bonded to the synthetic resin film 12 by the heat applied during the cross-linking of the silicone rubber composition 11. In this respect it is consequently possible for the cross-linking heat to be utilized at the same time for activation of the hot-melt adhesive.

The method may be particularly simplified as shown in FIG. 2 if the holding element 14, to which the adhesive layer 15 is applied, is positioned by means of a corresponding cooperating member 18 to the mold cover 20 and the cooperating member 18 is arranged to align with the desired position on the inner side of the breast prosthesis after closing of the mold cover. During the application of heat during the cross-linking of the silicone rubber composition 11 the adhesive layer 15 is activated. The holding element 14 is detached from cooperating member 18 on the mold cover 20 after cross-linking by opening the mold cover.

The cooperating member 18 may be a loop component of a hook-and-loop fastener, and may be attached to the mold cover by a suitable adhesive which will not release under the heat required for curing the prosthesis.

I claim:

1. In a method for the production of a breast prosthesis comprising the following steps:
   introducing a two-component addition cross-linkable soft elastic silicone rubber composition into a synthetic resin film, which is to constitute the outer and inner side of the breast prosthesis,
   introducing the uncross-linked silicone rubber composition into a mold, and
   cross-linking said silicone-rubber composition by heating said mold and said silicone rubber composition, the improvement comprising the step of:
   applying to the synthetic resin film constituting the inner side of the breast prosthesis at least one holding element, in the form of an adhesive strip, applied by the activation of a hot-melt adhesive, said hot-melt adhesive being cured during the step of cross-linking said silicone-rubber composition.

2. The method as claimed in claim 1, wherein the step of applying at least one holding element comprises applying one part of a two-part burr fastener tape.

3. The method as claimed in claim 1, further comprising the steps of positioning the holding element by means of a suitable cooperating member on a cover of the mold, closing the mold to move the holding element into a desired position on the inner side of the breast prosthesis, activating the hot-melt adhesive by heat provided during the cross-linking of the silicone rubber, and detaching the holding element from the cooperating member by opening the mold after the completion of the cross-linking.

4. The method as claimed in claim 1, wherein the synthetic resin film employed and furthermore the hot-melt adhesive include polyurethane.

5. The method as claimed in claim 1, wherein said holding element comprises an adhesive layer, said adhesive layer being adapted to be connected to a complementary support film, on which a permanent tacky layer is applied.

6. The method as claimed in claim 1 wherein the step of applying the holding element comprises covering over a large area of the inner side of the breast prosthesis with at least one holding element.

7. The method as claimed in claim 1, wherein the step of applying the holding element comprises covering over a marginal zone of the breast prosthesis with at least one holding element.

8. The method as claimed in claim 1, wherein the step of applying the at least one holding element comprises bonding a multiplicity of holding elements to a marginal zone of the inner side of the breast prosthesis.

9. The method as claimed in claim 1, wherein the step of applying the at least one holding element comprises bonding a multiplicity of holding elements to the entire area of the inner side of the breast prosthesis.

* * * * *